US009167958B2

(12) United States Patent
Banik et al.

(10) Patent No.: US 9,167,958 B2
(45) Date of Patent: *Oct. 27, 2015

(54) ENDOSCOPE HAVING AUTO-INSUFFLATION AND EXSUFFLATION

(75) Inventors: Michael S. Banik, Bolton, MA (US);
Lucien Alfred Couvillon, Jr., Concord, MA (US); Dennis R. Boulais, Danielson, CT (US); Anh Nguyen, Woburn, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1721 days.

This patent is subject to a terminal disclaimer.

(21) Appl. No.: 12/020,463

(22) Filed: Jan. 25, 2008

(65) Prior Publication Data
US 2008/0125629 A1    May 29, 2008

Related U.S. Application Data

(63) Continuation of application No. 10/926,712, filed on Aug. 26, 2004, now Pat. No. 7,335,159.

(51) Int. Cl.
A61B 1/015    (2006.01)
A61B 1/05     (2006.01)
A61B 1/31     (2006.01)
A61B 1/00     (2006.01)

(52) U.S. Cl.
CPC ............ *A61B 1/015* (2013.01); *A61B 1/00094* (2013.01); *A61B 1/051* (2013.01); *A61B 1/31* (2013.01); *A61B 1/00101* (2013.01)

(58) Field of Classification Search
CPC .. A61B 1/015; A61B 1/00101; A61B 1/0008; A61B 1/00094; A61B 1/051; A61B 1/31

USPC ................. 600/156–159, 129, 116, 105, 179
See application file for complete search history.

(56) References Cited

U.S. PATENT DOCUMENTS

| 3,850,162 | A |   | 11/1974 | Iglesias |         |
|-----------|---|---|---------|----------|---------|
| 4,869,238 | A | * | 9/1989  | Opie et al. | 600/109 |
| 4,878,893 | A |   | 11/1989 | Chin |         |
| 4,924,853 | A | * | 5/1990  | Jones et al. | 600/111 |
| 4,950,278 | A |   | 8/1990  | Sachse |         |
| 4,971,034 | A | * | 11/1990 | Doi et al. | 600/104 |
| 4,998,972 | A |   | 3/1991  | Chin |         |
| 5,139,478 | A |   | 8/1992  | Koninckx |         |
| 5,191,878 | A | * | 3/1993  | Iida et al. | 600/157 |
| 5,320,091 | A | * | 6/1994  | Grossi et al. | 600/104 |
| 5,328,458 | A |   | 7/1994  | Sekino |         |
| 5,343,855 | A | * | 9/1994  | Iida et al. | 600/157 |
| 5,518,502 | A | * | 5/1996  | Kaplan et al. | 600/157 |
| 5,549,546 | A |   | 8/1996  | Schneider |         |
| 5,637,075 | A |   | 6/1997  | Kikawada |         |
| 5,688,222 | A | * | 11/1997 | Hluchy et al. | 600/156 |
| 5,738,630 | A | * | 4/1998  | Suzuki et al. | 600/121 |
| 5,800,381 | A |   | 9/1998  | Ognier |         |

(Continued)

*Primary Examiner* — John P Leubecker
(74) *Attorney, Agent, or Firm* — Bookoff McAndrews, PLLC

(57) ABSTRACT

An endoscopic imaging system for examining a patient's body cavity includes an endoscope having a distal end, a proximal end and a number of lumens therein. One or more distal gas ports are disposed at or adjacent the distal end of the endoscope and one or more proximal gas ports are disposed proximal to the distal gas ports. Insufflation gas is delivered to the distal gas ports and withdrawn from the proximal gas ports or vice versa such that a gas bubble is formed in the body cavity and travels with the distal tip of the endoscope.

18 Claims, 6 Drawing Sheets

(56) References Cited

U.S. PATENT DOCUMENTS

| | | |
|---|---|---|
| 5,807,240 A * | 9/1998 | Muller et al. ............... 600/135 |
| 5,823,947 A | 10/1998 | Yoon |
| 5,830,126 A | 11/1998 | Odanaka |
| 5,922,004 A * | 7/1999 | DuBois ....................... 606/190 |
| 6,007,482 A | 12/1999 | Madni |
| 6,095,971 A * | 8/2000 | Takahashi ................... 600/159 |
| 6,196,966 B1 | 3/2001 | Kerin |
| 6,533,722 B2 * | 3/2003 | Nakashima .................. 600/179 |
| 6,645,140 B2 * | 11/2003 | Brommersma ............... 600/128 |
| 7,150,713 B2 | 12/2006 | Shener |
| 7,413,543 B2 * | 8/2008 | Banik et al. ................... 600/129 |
| 2002/0143239 A1 * | 10/2002 | Henzler ....................... 600/179 |
| 2003/0065250 A1 | 4/2003 | Chiel |
| 2004/0143159 A1 | 7/2004 | Wendlandt |
| 2004/0193218 A1 * | 9/2004 | Butler ............................. 607/1 |
| 2004/0199052 A1 * | 10/2004 | Banik et al. ................... 600/142 |
| 2005/0203342 A1 | 9/2005 | Kucklick |
| 2006/0116553 A1 | 6/2006 | Dunki-Jacobs |

\* cited by examiner

ENDOSCOPE HAVING AUTO-INSUFFLATION AND EXSUFFLATION

This application is a continuation of application Ser. No. 10/926,712, filed Aug. 26, 2004, which is now U.S. Pat. No. 7,335,159, which is incorporated herein by reference.

FIELD OF THE INVENTION

The present invention relates to an automatic medical insufflation device for diagnostic and surgical endoscopy. In particular, it relates to a system for and method of creating and controlling an observation space within a human body cavity so as to optimize diagnostic and/or surgical endoscopy by insufflation.

BACKGROUND OF THE INVENTION

Endoscopes have been used in the medical field for many years to look within a selected region of a patient's body, e.g., the colon. The endoscope is typically inserted through an orifice or a surgical incision into a body channel or cavity. Endoscopes are commonly used to perform surgical, therapeutic, diagnostic, or other medical procedures under direct visualization. Conventional endoscopes generally contain several endoscope components, including illuminating means such as light-emitting diodes or fiber optic light guides connected to a proximal source of light, imaging means such as a miniature video camera or a fiber optic image guide, and a working channel. Flexible endoscopes incorporate an elongated flexible shaft and an articulating distal tip to facilitate navigation through the internal curvature of a body cavity or channel. Examples of conventional endoscope designs are described in U.S. Pat. No. 4,706,656, U.S. Pat. No. 4,911,148, and U.S. Pat. No. 5,704,899.

Typical endoscopes provide a conduit for the delivery of an inert gas to insufflate the colon to facilitate examination. The colon, which collapses upon itself when empty, must be inflated to create a space, thereby creating a clear field of view for visualization. In order to insufflate the colon, conventional endoscopic systems utilize an air compressor or other similar gas supply sources. Insufflation creates a space for visualization and keeps the gas pressure constant within the colon by controlling the pressure of the gas supply by means of valves, pressure regulators, and other control devices.

In a standard endoscopic procedure, an operator actively monitors and manually maintains set-point pressure and flow values by checking the displays and operating the controls of the insufflation device. Because many systems do not provide quantitatively accurate methods of regulating the delivery of the gas, those systems can allow variations in the pressure, volume, and flow rate of gas administered during an endoscopic procedure.

In addition, air pressure in the colon is a cause of pain for the patient, both during the procedure and afterwards, due to distension of the bowel if the pressure is not abated. Furthermore, excess insufflation pressure can potentially stress, or even rupture, the colon during the colonoscopy or may cause the development of late perforations if the pressure and volume of the insufflating gas is not accurately controlled and promptly released.

SUMMARY OF THE INVENTION

To address the problems associated with conventional endoscopic insufflation systems, the present invention decreases patient discomfort due to insufflation of a body lumen and allows a physician a clear field of view of an interior body cavity. The present invention automatically controls insufflation and exsufflation parameters based on different operating modes of the system and/or based on body cavity characteristics viewed by the endoscope. In one embodiment, the present invention is an endoscopic imaging system of the type that includes an elongated shaft having a proximal end and a distal end. The shaft includes one or more distal gas ports at or adjacent the distal end of the shaft and one or more proximal gas ports. The endoscope is removably connected to a control unit having an insufflation gas supply and a gas venting system. Insufflation gas is selectively delivered to the distal gas ports and withdrawn from the proximal gas ports or vice versa during an endoscopic examination so that a gas bubble is formed around the distal end of the endoscope. The gas bubble travels with the distal tip as the endoscope is inserted into or withdrawn from the lumen.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

As indicated above, the present invention is an endoscopic imaging system that performs automated insufflation for use with diagnostic and surgical endoscopy. Although the present invention is described with respect to its use within the colon, it will be appreciated that the invention can be used in any body cavity that can be expanded for examination and/or surgery.

Figure 1:
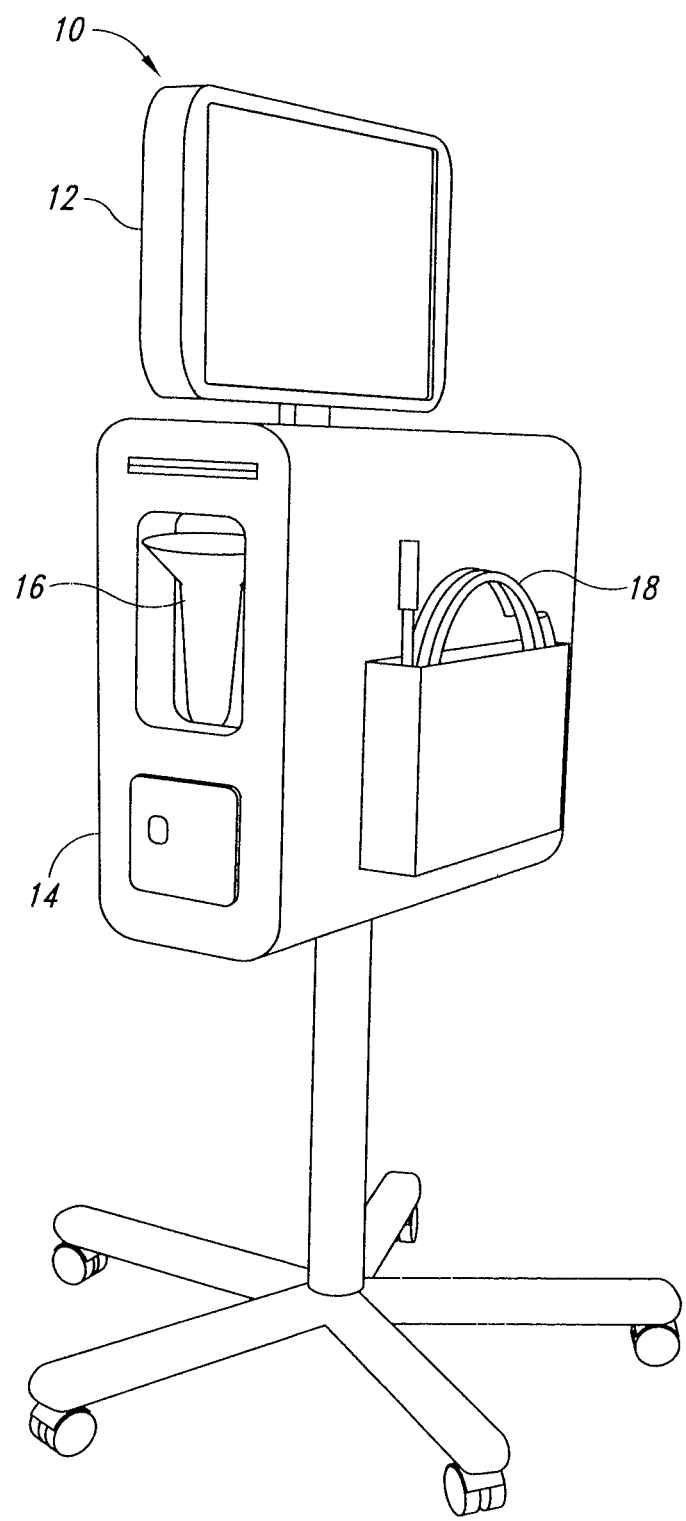
FIG. 1 illustrates a single-use endoscopic imaging system in accordance with one embodiment of the present invention.

FIG. 1 illustrates the major components of an exemplary single-use endoscopic imaging system 10. The components of the system 10 include a display 12, a user input device 16, and a single-use imaging endoscope 18, all of which are functionally connected to a control cabinet 14 that executes application software (not shown) residing therein. Display 12 is any special-purpose or conventional computer display device, such as a computer monitor, that outputs graphical images and/or text to a user. Single-use imaging endoscope 18 is a single-use flexible tube that contains one or more lumens for the purpose of performing endoscopic procedures and facilitating the insertion and extraction of fluids, gases, and/or medical devices into and out of the body. Single-use endoscope 18 further contains a digital imaging system (not shown) comprised of, in one example, an image sensor such as a CMOS imager, optical lenses such as plastic optics, a light source such as a number of LEDs, and an articulating tip that enables steering of the endoscope in a desired direction.

Control cabinet 14 is a special-purpose electronic and electro-mechanical apparatus that processes and manages all system functions, and includes a network-enabled image-processing CPU, a physical connection to the single-use endoscope 18, an optional dock for the user interface 16, and valves that control the delivery of gas/water to the endoscope and a vacuum line that removes the air/gas and debris, etc., from the patient. User input device 16 is a hand-held device, either wired to the control cabinet 14 or wireless, that accepts inputs from a human operator via standard push buttons, joysticks, or other activation devices either singularly or in combination to control the operation of single-use endoscopic imaging system 10.

Operation of single-use endoscopic imaging system 10 is as follows: the system is initiated and operated upon command by means of user input device 16, causing the application software executed by a processor within the control cabinet 14 to activate the appropriate hardware to perform surgical, therapeutic, diagnostic, or other medical procedures and to deliver insufflation and/or suction to the lumen(s) of single-use endoscope 18. Display 12 provides live endoscopic video images and visual feedback of control parameters to the physician or operator so that an examination of the patient can be completed. Upon termination of the examination, the endoscope 18 is disconnected from the control cabinet and disposed of.

Figure 2:
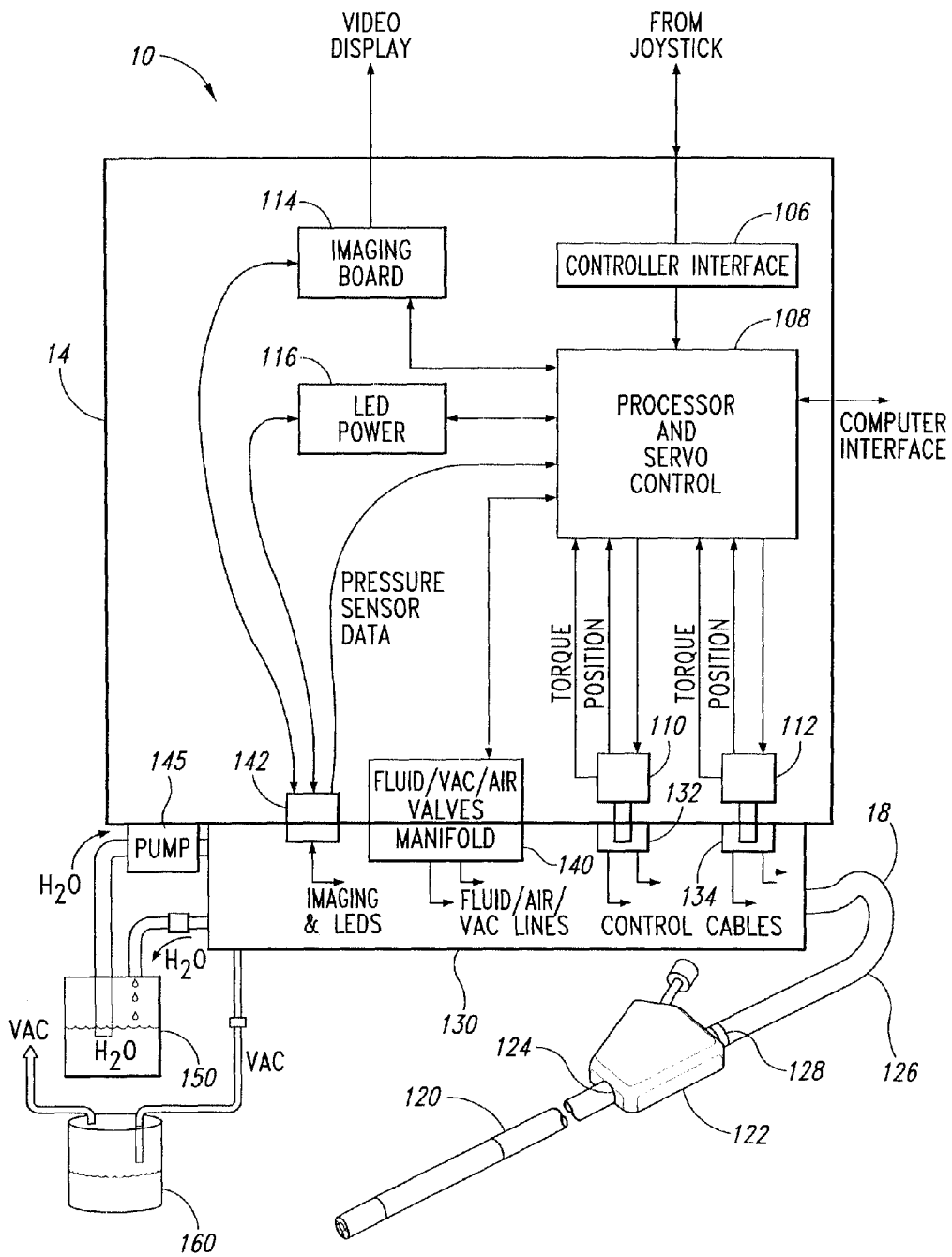
FIG. 2 is a functional block diagram that shows the interrelationship of the major components of a single-use endoscopic imaging system shown in FIG. 1.

FIG. 2 is a functional block diagram of single-use endoscopic imaging system 10 that shows the operational interrelationship of the major hardware and software elements of the system. A complete description of the control cabinet 14 and other components is set forth in U.S. patent application Ser. No. 10/811,781, filed Mar. 29, 2004, and is herein incorporated by reference. The single-use endoscopic imaging system 10 includes the control cabinet 14 that operates to control the orientation and functions of a single-use imaging endoscope 18. The control cabinet 14 includes a controller interface 106 that receives commands from the user input device such as a joystick, that is used by a physician or their assistant to control the operation of the single-use imaging endoscope. Commands from the joystick are supplied to a programmable processor such as a digital signal processor that controls the overall operation of the imaging system and a servo control unit 108. The processor and servo control unit 108 control the operation of a pair of servo motors 110, 112 that in turn drive control cables within the single-use endoscope 18. The orientation of the distal tip is controlled in response to directional signals received from the user input device as well as feedback signals obtained from sensors that measure the position and torque of each of the servo motors 110, 112.

In one embodiment of the invention, the processor and servo control unit 108 implement a position-to-rate control that varies the speed at which the distal tip is moved as a function of the position of the directional switch on the user input device. However, other control algorithms such as position-to-position or position-to-force (i.e., acceleration) could also be implemented.

The control cabinet 14 also includes an imaging board 114 that produces images from the signals that are received from the image sensor at the distal end of the single-use endoscope 18. The imaging board 114 deserializes the digital video signal from the CMOS imager and performs the necessary algorithms such as demosaicing, gain control and white balance to produce a quality color image. The gain control of the system is implemented by adjusting the intensity of the illumination (current supplied to a number of LEDs) and adjusting the RGB gains to the CMOS imager. The imaging board 114 also includes isolation circuitry to prevent a patient from becoming shocked in the event of an electrical failure on the imaging board 114 or within the control cabinet 14 as well as circuitry for transmitting control signals to the image sensor and for receiving image signals from the image sensor. In one embodiment of the invention, the imaging board 114 is provided on a standard PC circuit board to allow individual endoscopes to be tested with a personal computer and without the need for an additional control cabinet 14.

In the embodiment shown in FIG. 2, the single-use endoscope 18 has a distal shaft portion 120 that is connected to a breakout box 122 with a swivel connection 124. In addition, the proximal portion 126 of the shaft is connected to the breakout box 122 with a second swivel connection 128. The swivel connections 124, 128 allow the distal and proximal ends of the endoscope to rotate with respect to the breakout box 122 and without twisting the breakout box 122 in the hands of the physician or their assistant.

In the embodiment shown, the single-use endoscope 18 is connected to the control cabinet 14 with a connector 130. Within the connector 130 are a pair of spools 132, 134 that are engageable with the driveshafts of the servo motors 110, 112. Each spool 132, 134 drives a pair of control cables in opposite directions. One pair of control cables drives the distal tip of the endoscope in the tip and down direction, while the other pair of control cables drives the distal tip of the endoscope in the left and right direction.

The connector 130 also includes a manifold 140 that controls the supply of fluid, air and vacuum to various tubes or lumens within the endoscope 18. In addition, the connector 130 includes an electrical connector 142 that mates with the corresponding electrical connector on the control cabinet 102. The connector 142 transfers signals to and from the image sensor as well as power to the illumination LEDs and allows connection to a thermal sensor at the distal end of the endoscope. In addition, the connector 142 carries signals from a remote pressure sensor as will be described below. Water or another liquid is supplied to the endoscope with a pump 145. The pump 145 is preferably a peristaltic pump that moves the water though a flexible tube that extends into the proximal connector 130. Peristaltic pumps are preferred because the pump components do not need to come into contact with the water or other fluids within the endoscope and it allows the wetted component to be single-use. A water reservoir 150 connected to the pump 145 supplies water to cool the illumination LEDs as well as to irrigate the patient. The water supplied to cool the LEDs is returned to the reservoir 150 in a closed loop. Waste water or other debris are removed from the patient with a vacuum line that empties into a collection bottle 160. Control of the vacuum to the collection bottle 160 is provided at the manifold 140 within the proximal connector 130. A gas source provides insufflation by delivering an inert gas such as carbon dioxide, nitrogen, air, etc., to the lumen(s) of single-use endoscope 18 via the manifold 140.

The processor and control unit 108 executes application software, including GUI software application, system control software application, and a network software application that reside on a computer readable medium such as a hard disc drive, CD-ROM, DVD, etc., or in a solid state memory. GUI software application is well known to those skilled in the art, and provides the physician or operator with live endoscopic video or still images and, optionally, with visual, audible, or haptic control and feedback on display 12 using user input device 16. System control software application is the central control program of application software that receives input from sensors, such as from a pressure sensor as described below, and from the user input device 16. System control software application provides system control for the functions necessary to operate single-use endoscope system 10. The network software application operates a network connection to allow the endoscopic imaging system 10 to be connected to a local area network and/or the Internet.

As set forth in the Ser. No. 10/811,781 application, the manifold 140 supplies insufflation gas, water and vacuum to one or more lumens of single-use endoscope 18. The manifold is preferably constructed as a series of passages that are formed between sheets of a thermoplastic material. Water, air, and vacuum are applied to inputs of the manifold and selectively delivered to outputs that are in turn connected to lumens within the endoscope 18 by pinch valves on the control cabinet 14 that open or close the passages in the manifold. The passages are preferably formed by rf welding the sheets of thermoplastic into the desired pattern of the passages.

Figure 3:
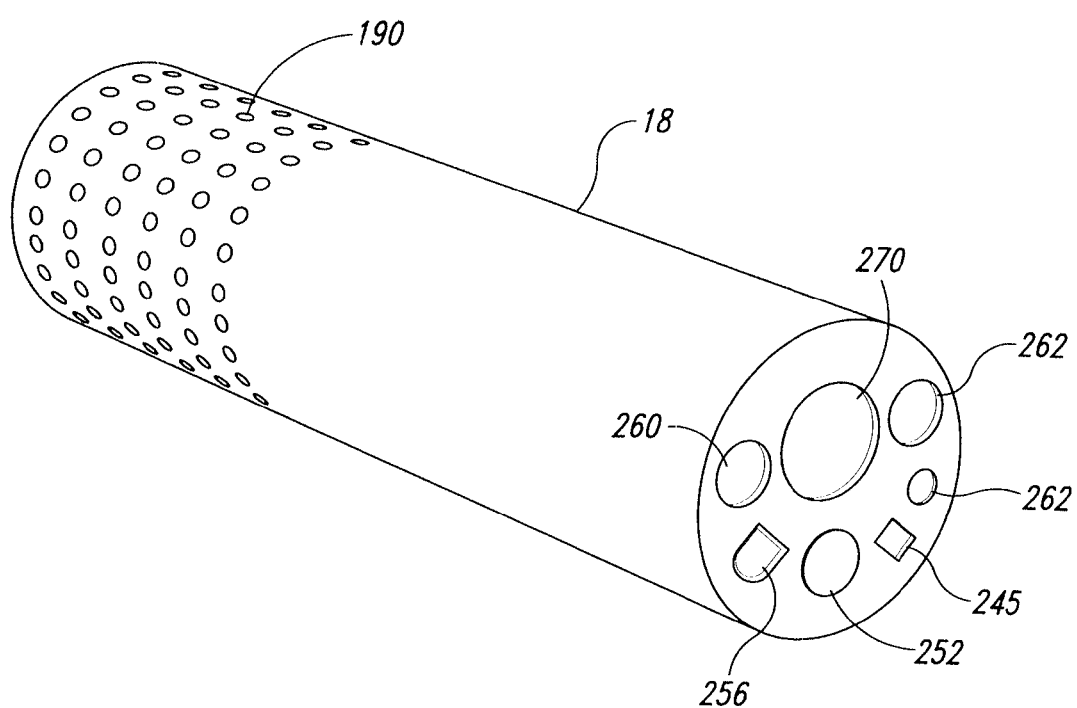
FIG. 3 illustrates a distal end of a single-use imaging endoscope in accordance with an embodiment of the present invention.

In accordance with FIG. 2, the basic process of insufflation and exsufflation using single-use endoscopic imaging system 10 is as follows:

During operation, live endoscopic video images are provided on display 12 by the GUI software application, which processes information from the imaging board 114, and the single-use endoscope 18. Prior to operation, insufflation is initiated upon operator command by means of the user input device 16. As a result, system control software application activates the manifold 140 by means of the pinch valves on the control cabinet 14. Upon advancing single-use endoscope 18, an insufflation gas is channeled through a dedicated lumen 175 of single-use endoscope 18 and into the patient. In one embodiment of the invention, as shown in FIG. 3, the gas delivery lumen terminates at directional port 256, that directs the insufflation gas and/or water over a lens 270 of the imaging sensor. As the distal tip of single-use endoscope 18 is advanced into the colon during the endoscopic procedure, further areas of the colon are insufflated, bringing new examination regions into view.

As single-use endoscope 18 is advanced through the colon, the region of the previous field of view is simultaneously exsufflated (collapsed), by connecting the vacuum source to one or more proximal gas ports 190 that exit on the exterior of the endoscope shaft and are positioned proximal to the distal gas port(s). The proximal gas ports 190 are connected through a dedicated lumen, or through the "free space" within the shaft of single-use endoscope to the proximal end of the endoscope. To collapse the gas bubble, the manifold 140 is activated by a pinch valve to apply vacuum through the one or more proximally located gas ports 190. By this means, the body cavity is deflated directly behind the tip of single-use endoscope 18, thus forming a traveling insufflation bubble within the body cavity.

Figure 4:
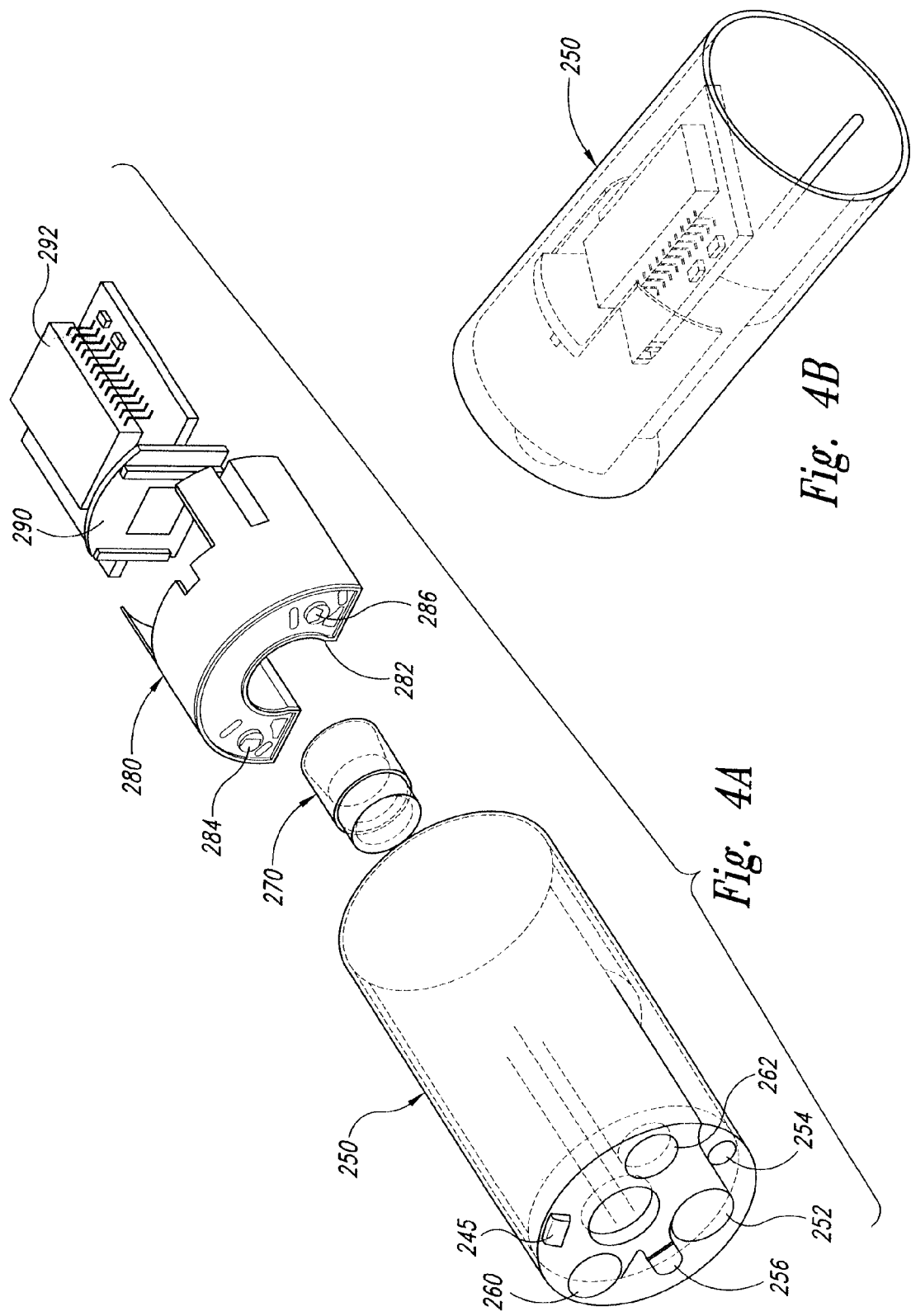
FIGS. 4A and 4B illustrate an imaging sensor and heat exchanger positioned at the distal end of the endoscope in accordance with an embodiment of the present invention.

As shown in FIG. 4A, the distal end of the single-use endoscope 18 includes a distal cap 250 having a number of openings on its front face. The openings include an opening to a working channel 252 and an opening 254 for a low pressure lavage, whereby a stream of liquid can be delivered through the endoscope for removing debris or obstructions from the patient. A lens wash and insufflation port includes an integrated flush cap 256 that directs water across the lens of an image sensor and delivers the insufflation gas to expand the lumen in which the endoscope is inserted. Offset from the longitudinal axis of the endoscope is a lens port 258 that is surrounded by a pair of windows or lenses 260 and 262 that cover the illumination sources. An optional pressure sensor 245 is also disposed on or adjacent the front face of the distal cap 250 to detect pressure within the body cavity of the patient. Signals from the pressure sensor 245 are transmitted back to the processor and servo control unit 108 through the electrical connector 142. A suitable pressure sensor 245 is a miniature pressure gauge available from National Semiconductor Corporation or Konigsberg Instruments, Inc.

As best shown in FIG. 4A, the imaging assembly also includes a heat exchanger 280. The heat exchanger 280 comprises a semi-circular section having a concave recess 282 into which a cylindrical lens assembly 270 is fitted. The concave recess 282 holds the position of the lens assembly 270 in directions perpendicular to the longitudinal axis of endoscope, thereby only permitting the lens assembly 270 to move along the longitudinal axis of the endoscope. Once the lens assembly is positioned such that it is focused on an image sensor 290 that is secured to a rear surface of the heat exchanger 280, the lens assembly is fixed in the heat exchanger with an adhesive. A pair of LEDs 284, 286 are bonded to a circuit board that is affixed in the heat exchanger such that a channel is formed behind the circuit board for the passage of a fluid or gas to cool the LEDs. A circuit board or flex circuit 292 containing circuitry to transmit and receive signals to and from the control cabinet is secured behind the image sensor 290 and to the rear surface of the heat exchanger 280. With the lens assembly 270, the LEDs 284, 286, the image sensor 290, and associated circuitry 292 secured in the heat exchanger 280, the heat exchanger assembly can be fitted within the distal cap 250 to complete the imaging assembly.

Figure 5:
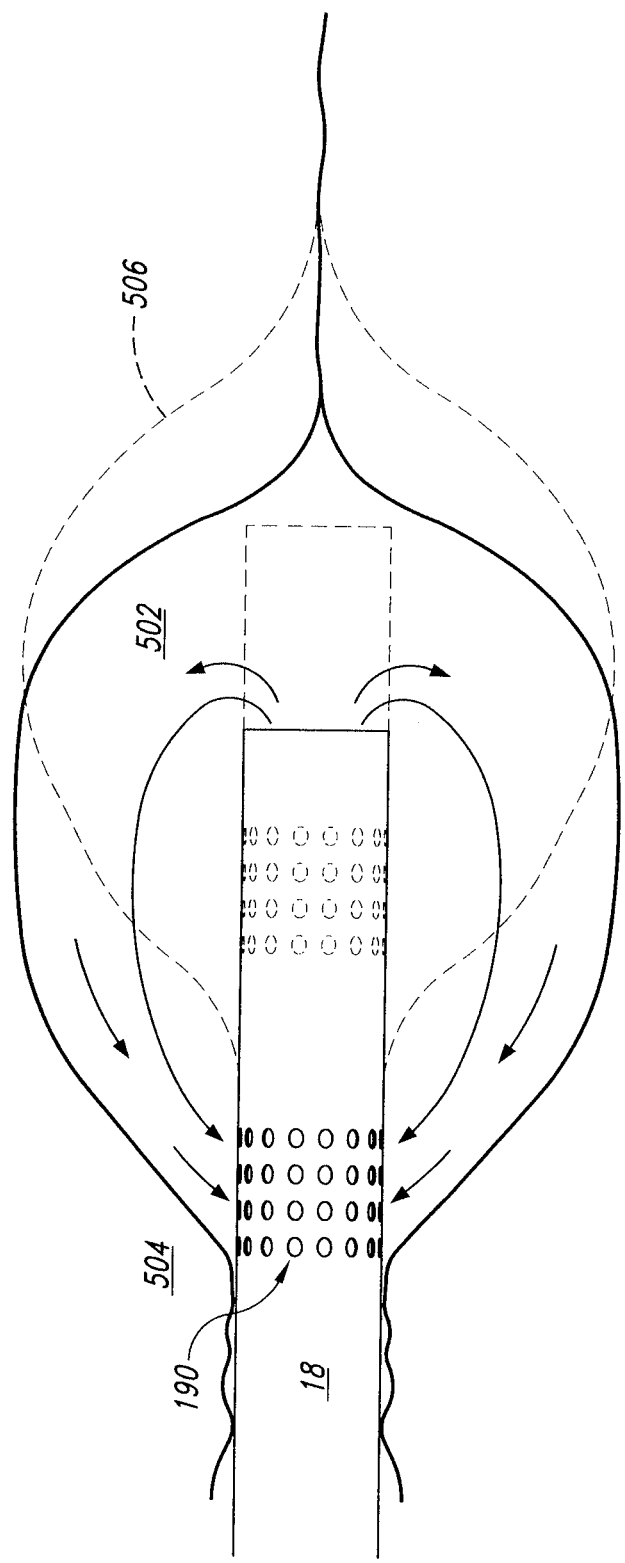
FIG. 5 illustrates a gas bubble created by the present invention that moves with the distal tip of an endoscope.

FIG. 5 illustrates a single-use endoscope 18 that is inserted into a body cavity such as a colon. As the single-use imaging endoscope 18 is advanced, gas is delivered through the one (or more) distal gas insufflation ports to inflate a bubble 502 surrounding the distal end of the single-use imaging endoscope 18. Gas is withdrawn from the proximal gas exsufflation ports 190 to collapse the colon at an area 504 proximal to the distal end of the endoscope 18. As the endoscope 18 is moved distally, the bubble moves distally, as indicated by bubble 506 as shown in phantom lines.

When retracting the endoscope during the examination, the operator enters the appropriate command on user interface 116, whereby the system electronics cause the manifold 140 to reverse the functions of the proximal and distal gas ports at the tip of single-use endoscope 18. That is, insufflation gas is supplied to the proximal gas ports 190 and vacuum is applied to the distal insufflation ports or another port such as the entrance to the working channel (not shown) located at or adjacent the distal tip of single-use endoscope 18.

As indicated above, the distal end of the single-use endoscope 18 includes an optional pressure sensor 245 that allows the processor and servo control 108 in the control cabinet 14 to regulate the pressure of the insufflation to provide a clear field of view while reducing patient discomfort and lessening the likelihood of potential injury.

Figure 6:
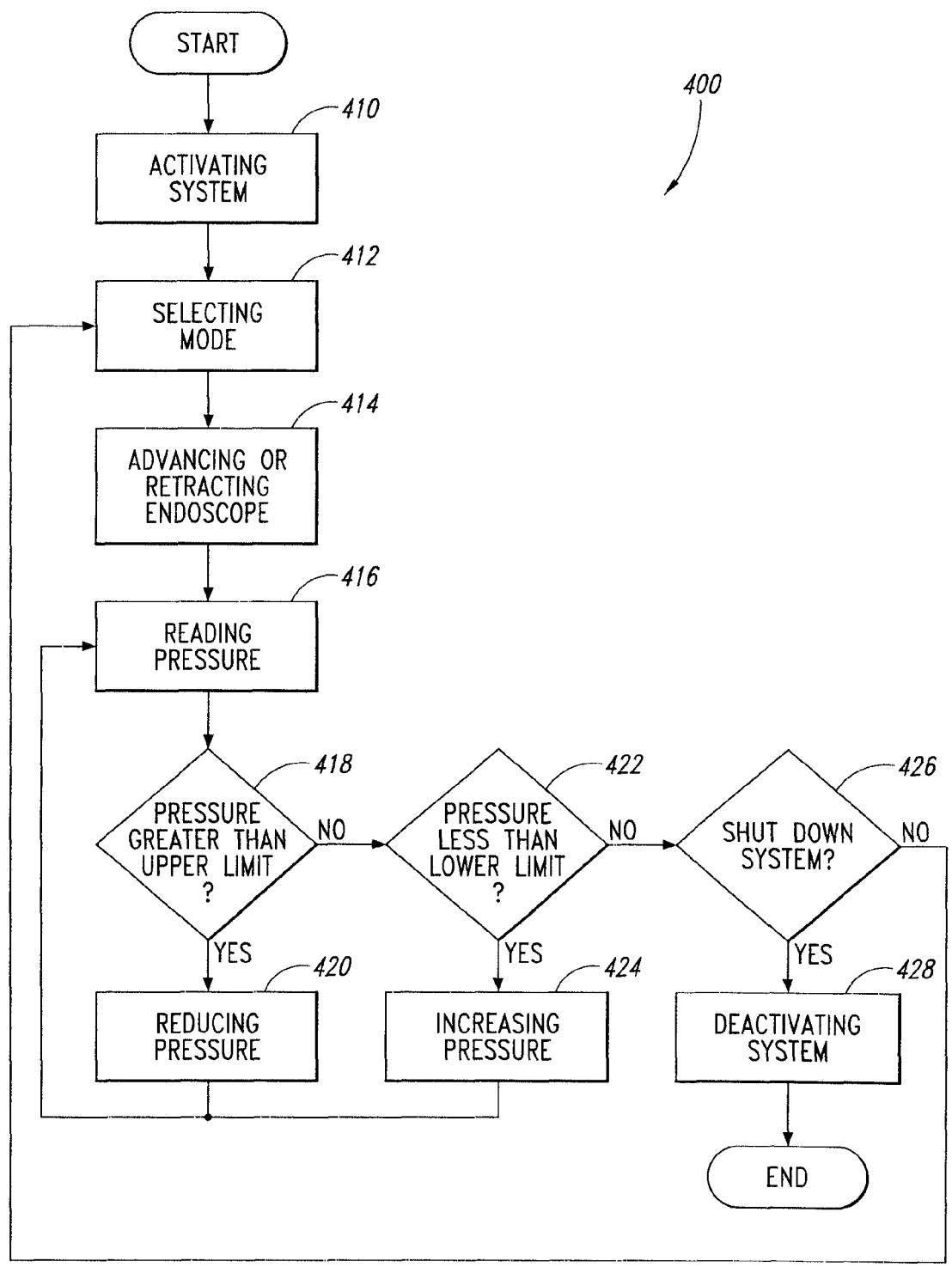
FIG. 6 is a flow diagram of an exemplary method of insufflation and exsufflation using the single-use imaging endoscope in accordance with the present invention.

FIG. 6 is a flow diagram of a method 400 for the process of insufflation and exsufflation using a single-use imaging endoscope 18 in the single-use endoscopic imaging system 10 of the present invention. FIGS. 1 through 3 are referenced throughout the steps of method 400. Method 400 includes the following steps:

Step 410: Activating System

In this step, operation of single-use endoscopic imaging system 10 begins. The operator activates insufflation via user interface 16. Method 400 proceeds to step 412.

Step 412: Selecting Mode

In this step, the operator selects an endoscopic operating mode via user interface 16 based on whether the operator is advancing or retracting single-use endoscope 18 within the colon. During operation, if the operator does not change the operating mode, the system maintains its current operating mode. Method 400 proceeds to step 414.

Step 414: Advancing or Retracting Endoscope

In this step, system control software activates manifold 140, through the control of systems electronics. If the operator chose the advancing mode in step 412, manifold 140 connects an insufflation gas source to the distal gas port and connects a vacuum line to proximal gas ports 190 adjacent the distal end of single-use endoscope 18 or vents the proximal gas ports to the atmosphere. If the operator chose the retracting mode in step 412, manifold 140 connects insufflation gas source to the proximal gas ports 190 and connects the vacuum line to the distal gas port at the distal end of single-use endoscope 18 or vents the distal gas port to the atmosphere. Method 400 proceeds to step 416.

Step 416: Reading Pressure

In this step, system electronics samples the output of pressure sensor 245. Pressure sensor 245 measures the insufflation pressure in the colon. The resultant pressure data is passed to the system control software. Method 400 proceeds to step 418.

Step 418: Pressure Greater than Upper Limit?

In this decision step, system control software compares the insufflation pressure read in step 416 with a predefined maximum limit in the range of 0.1 to 0.5 atmospheres 2-4 psig and determines whether the pressure read in step 416 exceeds this limit. If yes, method 400 proceeds to step 420; if no, method 400 proceeds to step 422.

Step 420: Reducing Pressure

In this step, system control software commands manifold 140, to stop or reduce the flow of insufflation inert gas to distal end 300 of single-use endoscope 18. Method 400 returns to step 416.

Step 422: Pressure Less than Lower Limit?

In this decision step, system control software application 222 compares the insufflation pressure read in step 416 with a predefined minimum limit in the range of 2-4 psig, and determines whether the pressure read in step 416 is below this limit. If yes, method 400 proceeds to step 424; if no, method 400 proceeds to step 426.

Step 424: Increasing Pressure

In this step, system control software activates manifold 140, to begin or increase the flow of insufflation inert gas to the distal end of single-use endoscope 18. Method 400 returns to step 416.

Step 426: Shut Down System?

In this decision step, system control software determines whether insufflation has been deactivated by operator command via user interface 16. If yes, method 400 proceeds to step 428; if no, method 400 returns to step 412.

Step 428: Deactivating System

In this step, system control software commands manifold 140 to close the inert gas source and vacuum line from the distal end of the single-use endoscope 18. Method 400 ends.

While the preferred embodiment of the invention has been illustrated and described, it will be appreciated that various changes can be made therein without departing from the scope of the invention. For example, control of the insufflation gas delivered to the patient may be based on other sensed signals besides the pressure detected. Maximum gas pressure and/or flow rate of the gas can be selected by the physician by viewing images on the display screen or by taking into consideration depth of insertion of the endoscope, rate of change in gas pressure, age, sex, size of the patient, etc. It is therefore intended that the scope of the invention be determined from the following claims and equivalents thereto.

The embodiments of the invention in which an exclusive property or privilege is claimed are defined as follows:

1. An endoscope comprising:
   an elongate member having a proximal end and a distal end and defining a plurality of lumens;
   one or more first ports disposed at or adjacent to a distal end of the endoscope and connected to a source of gas or liquid;
   one or more second ports formed in the elongate member at an axial position proximal of the one or more distal ports;
   a controller including a processor configured to deliver gas or liquid to the one or more first ports while applying suction to the one or more second ports; and
   a manifold, wherein the manifold is configured to reverse the delivery of gas or liquid and the application of suction so that the one or more first ports is applying suction while the one of more second ports is delivering gas or liquid.

2. The endoscope of claim 1, wherein the endoscope includes an imaging assembly.

3. The endoscope of claim 2, wherein the one or more first ports are positioned proximate the imaging assembly.

4. The endoscope of claim 1, wherein the one or more second ports are in fluid communication with one of the plurality of lumens of the elongate member.

5. The endoscope of claim 1, further comprising a user input device, wherein the controller is configured to receive commands from the user input device.

6. The endoscope of claim 5, wherein the processor is configured to receive the commands from the user input device.

7. The endoscope of claim 1, wherein the processor is configured to implement a position-to-rate control.

8. The endoscope of claim 1, wherein the controller is further configured to regulate pressure.

9. The endoscope of claim 1, further comprising a pressure sensor.

10. An endoscope, comprising:
    an elongate member;
    a cap provided at a distal end of the elongate member, the cap defining a first set of ports, wherein the cap includes an imaging assembly, and wherein a proximalmost end of the imaging assembly is distal to the distal end of the elongate member;
    a second set of ports disposed proximal to the first set of ports;
    a controller configured to deliver gas or liquid to one of the first and second set of ports while applying suction to the other of the first and second set of ports and regulate pressure at the distal end of the elongate member; and
    a manifold, wherein the manifold is configured to reverse the delivery of gas or liquid and the application of suction so that the one or more first ports is applying suction while the one of more second ports is delivering gas or liquid.

11. The endoscope of claim 10, wherein the first set of ports is formed in a distal facing surface of the cap.

12. The endoscope of claim 10, wherein the first set of ports is offset from a longitudinal axis of the elongate member.

13. The endoscope of claim 10, wherein the second set of ports is distributed around a circumference of the elongate member.

14. An endoscope, comprising:
    an elongate member;

a first set of ports in communication with one or more lumens extending from a proximal end of the elongate member;

a second set of ports disposed proximal to the first set of ports, wherein one of the first and second set of ports is configured to deliver gas as a vacuum is applied to the other of the first and second set of ports;

a pressure sensor at a distal end of the elongate member; and a manifold, wherein the manifold is configured to reverse the delivery of gas or liquid and the application of suction so that the one or more first ports is applying suction while the one of more second ports is delivering gas or liquid.

15. The endoscope of claim 14, further including an imaging assembly, wherein the imaging assembly includes:

one or more illumination sources;

a cooling channel for removing heat from the illumination sources;

a bore adapted to accommodate one or more imaging lenses; and an image sensor, wherein the distally facing end surface includes a plurality of windows positioned in front of the illumination sources.

16. An endoscope for insertion into a body cavity of a patient, comprising:

an elongate member having a proximal end and a distal end;

one or more first ports disposed at or adjacent to the distal end of the elongate member, the one or more first ports being connected to a source of gas;

a second set of ports disposed proximal to the one or more first ports, wherein each of the one or more first ports is in fluid communication with a lumen of the elongate member that delivers gas to the one or more first ports as suction is applied to the second set of ports;

a controller configured to regulate pressure at the distal end of the elongate member; and a manifold, wherein the manifold is configured to reverse the delivery of gas or liquid and the application of suction so that the one or more first ports is applying suction while the one of more second ports is delivering gas or liquid.

17. The endoscope of claim 16, wherein the second set of ports is distributed around a circumference of the elongate member.

18. The endoscope of claim 16, wherein the one or more first ports are disposed in a cap extending distally from the distal end of the elongate member, wherein the cap includes an imaging assembly, and wherein the one or more first ports are positioned proximate the imaging assembly, and wherein a proximalmost end of the imaging assembly is distal to the distal end of the elongate member.

* * * * *